United States Patent [19]

Mohacsi

[11] 4,194,044

[45] Mar. 18, 1980

[54] PROCESS FOR PREPARING 3-PHENOXY MORPHINANS

[75] Inventor: Ernest Mohacsi, Nutley, N.J.

[73] Assignee: Hoffmann-La Roche Inc., Nutley, N.J.

[21] Appl. No.: 914,656

[22] Filed: Jun. 12, 1978

Related U.S. Application Data

[63] Continuation-in-part of Ser. No. 811,233, Jun. 29, 1977, Pat. No. 4,113,729, which is a continuation-in-part of Ser. No. 748,022, Dec. 6, 1976, abandoned.

[51] Int. Cl.$^2$ .......................................... C07D 217/20
[52] U.S. Cl. .................................... 546/146; 546/149; 260/559 P
[58] Field of Search ...................... 260/287 D, 289 D; 546/146, 149

[56] References Cited

U.S. PATENT DOCUMENTS

| | | | |
|---|---|---|---|
| 3,634,429 | 1/1972 | Leimgruber et al. | 260/289 D |
| 3,707,470 | 12/1972 | Sawa | 546/15 |

FOREIGN PATENT DOCUMENTS

| | | |
|---|---|---|
| 2030981 | 6/1978 | Fed. Rep. of Germany . |
| 6811979 | 2/1969 | Netherlands . |

OTHER PUBLICATIONS

Tomita, J. Pham. Soc. Japan 72, pp. 424–426 (1952). CA 47:6430b (1953).
Chem. Abst. 62 11788g & h (1965), Abst. of Japanese Pat. #30,289 ('64), issued Dec. 25, 1964.
Chem. Abst. 59 10009a–g (1963), Abst. of Japanese Pat. #11,127('62), issued Aug. 5, 1962.

*Primary Examiner*—Alton D. Rollins
*Assistant Examiner*—D. B. Springer
*Attorney, Agent, or Firm*—Jon S. Saxe; Bernard S. Leon; William H. Epstein

[57] ABSTRACT

The preparation of 3-phenoxy N-substituted morphinans, useful as analgesics from 1-(p-hydroxybenzyl)-1,2,3,4,5,6,7,8-octahydroisoquinoline or cyclohexen-(1)-yl-ethylamine and p-phenoxyphenylacetic acid is described.

6 Claims, No Drawings

PROCESS FOR PREPARING 3-PHENOXY MORPHINANS

CROSS REFERENCE TO RELATED APPLICATIONS

This application is a continuation-in-part of U.S. Pat. application Ser. No. 811,233 filed June 29, 1977, now U.S. Pat. No. 4,113,729, issued Sept. 12, 1978 which in turn is a continuation-in-part of U.S. Pat. application Ser. No. 748,022, filed Dec. 6, 1976, now abandoned.

SUMMARY OF INVENTION

In U.S. Pat. Application Ser. No. 811,233, Mohacsi, filed July 29, 1977, there is disclosed levo-rotary compounds of the formula:

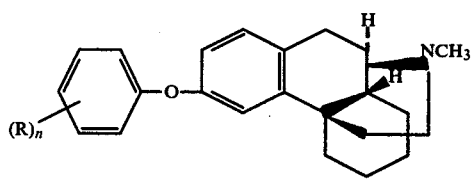

wherein R is halo, lower alkyl, nitro, lower alkoxy, hydroxy or hydrogen; n is an integer from 1 to 5; and pharmaceutically acceptable salts thereof which are useful as pain killing analgesics. In accordance with this invention, there is disclosed a method for producing the racemate of the compound of formula I, i.e. a compound of the formula

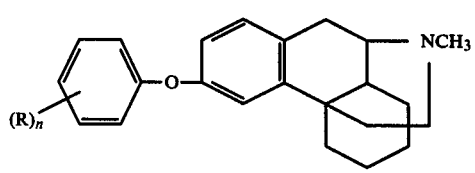

wherein R and n are as above from either reacting a compound

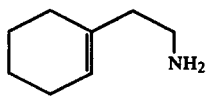

with a compound of the formula:

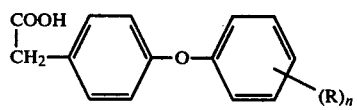

wherein R and n are as above or from a compound of the formula.

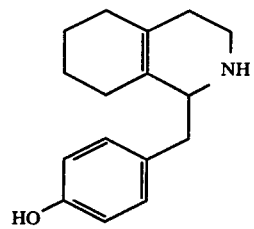

The racemate of formula I-A can be resolved to produce the compound of formula I. Also the compound of formula I-A and its pharmaceutically acceptable salts are useful as pain killing analgesics.

DETAILED DESCRIPTION OF THE INVENTION

As used herein, the term "halogen" includes all four halogens, i.e. bromine, chlorine, fluorine and iodine with fluorine and bromine being preferred. The term "lower alkyl" includes both straight and branched chain saturated aliphatic hydrocarbon groups containing from 1 to 7 carbon atoms, i.e. methyl, ethyl, n-propyl, isopropyl, n-butyl, isobutyl, etc. with methyl being preferred. The term "lower alkoxy" designates lower alkoxy groups containing from 1 to 7 carbon atoms such as methoxy, ethoxy, propoxy, isopropoxy, etc.

The compounds of formula I-A above form pharmaceutically acceptable acid addition salts with inorganic acids. Thus, the compounds of the present invention form pharmaceutically acceptable acid addition salts with inorganic acids such as hydrochloric acid, hydrobromic acid, sulfuric acid and phosphoric acid; and with organic acids such as tartaric acid, oxalic acid, citric acid, camphorsulfonic acid, ethanesulfonic acid, toluenesulfonic acid, salicylic acid, ascorbic acid, maleic acid, succinic acid, formic acid, acetic acid and the like.

The compounds of formula I-A and their pharmaceutically acceptable salts are useful as analgesics. These compounds, when administered orally or parentally, provide a relief from pain in the same manner as codeine. Furthermore, the compounds of this invention cannot be degraded chemically into compounds which have addiction liability such as dromoran.

The compounds of formula I-A and salts as herein described can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkyleneglycols and the like. The pharmaceutical preparations can be employed in a solid form, for example, as tablets, suppositories, capsules, or in liquid form, for example, as solutions, suspension or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The daily dose administered for the compounds will, of course, vary with the particular novel compounds employed because of the very potency of the compounds, the chosen route of administration and the size of the recipient. The dosage administered is not subject to definite bounds but it will usually be in effective amounts of the pharmacological function of the compound of formula I-A. Representative of a typical method for administering the compounds of formula I-A is by the oral type administration route. By this route, a tablet containing the compound of formula I-A can be administered orally at the rate of 0.1 microgram to 1.0 microgram per day per kilogram of body weight.

The compounds of formula I above and their salts are used as analgesic pain killing agents. This analgesic activity can be demonstrated in the standard phenylquinone writhing test (Sigmund et al., Proc. Soc. Exp. Biol. Med. 95:729 [1957]). The compounds of this invention significantly reduce pain and produce analgesic effects in mice exposed to intra-abdominally induced chemical pain. The $ED_{50}$ was the dose which reduced the total number of writhes by 50%. When the following compounds of formula I are utilized as the test substances, analgesic activity is observed as shown by the following $ED_{50}$ levels when compared to the standard analgesic agent codeine:

(−)-3-phenoxy-N-methylmorphinan tartrate-$ED_{50}$ 2.0 mg/kg (s.c.);
(±)-3-phenoxy-N-methylmorphinan oxalate $ED_{50}$ 0.42 mg/kg (s.c.); and
codeine $ED_{50}$ 3.9 mg/kg (s.c.).

In accordance with this invention are intermediates of the formula:

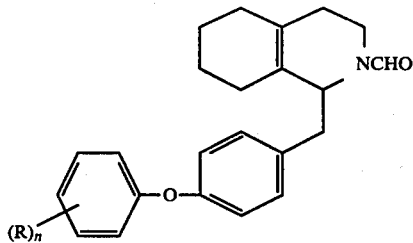

V wherein R and n are as above is produced by the reaction of a compound of formula II with a compound of formula III or by utilizing a compound of the formula IV.

The reaction of a compound of formula II with a compound of formula III produces a compound of the formula

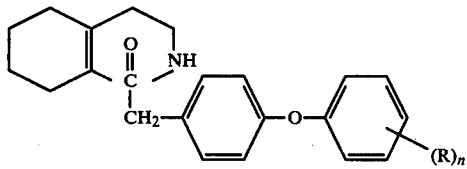

VI wherein R and n are as above.
The compound of formula VI is converted to the compound of formula V via the following intermediates:

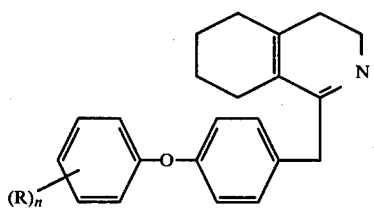

VII

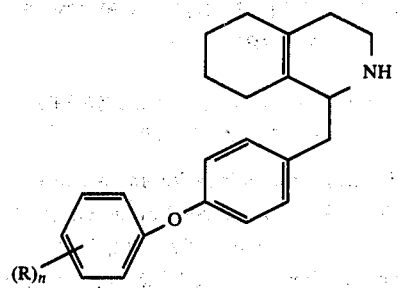

VIII wherein R and n are as above.

The compound of formula II is condensed with the compound of formula III to produce the compound of formula VI. Any conventional method of reacting an organic acid and an amine can be utilized to carry out this reaction. Among the preferred methods is to react the compound of formula II with the compound of formula III in the presence of an inert organic solvent while continuously removing water. Generally, this reaction is carried out in an inert organic solvent such as toluene or xylene, etc. at reflux temperature while removing water continuously. Any conventional method of removing water from the reaction medium can be utilized in carrying out this reaction.

The compound of formula VI is cyclized to the compound of formula VII by treatment with a phosphorous oxyhalide. Among the preferred cyclizing agents is included phosphorus oxyhalides such as phosphorus oxychloride. However, any conventional phosphorus oxyhalide can be utilized in carrying out this reaction. In general, this reaction can be carried out in the presence of an inert organic solvent. Any conventional inert organic solvent can be utilized. Among the preferred solvents are included xylene, toluene, benzene, as well as other conventional organic solvents. In carrying out this reaction, any temperature of from 80° C. to 275° C. can be utilized. Generally, it is preferred to carry out this reaction at the reflux temperature of the reaction medium. The compound of formula VII can be reduced to the compound of formula VIII by treatment with an alkali metal aluminum hydride or an alkali metal borohydride. Any conventional alkali metal aluminum hydride or alkali metal borohydride reducing agent can be utilized in carrying out this reduction. Among the preferred reducing agents for carrying out this reaction are included lithium aluminum hydride or a di(lower alkyl) aluminum hydride such as diisobutyl aluminum hydride. Any conventional alkali metal borohydride reducing agent can be utilized such as sodium borohydride, potassium borohydride, lithium borohydride. Any of the conditions conventional in utilizing these aluminum hydride or alkali metal borohydride reducing agents can be utilized to carry out this reduction reaction.

Generally, this reaction can be carried out without isolating the compounds of formula VII after removal of solvent and excess of reagent. In carrying out this reaction, any conventional inert organic solvent can be utilized. Among the preferred solvents are the lower alkanols such as methanol, ethanol, isopropanol, etc. In carrying out this reaction, temperature and pressure are not critical and this reaction can be carried out at room temperature and atmospheric pressure. On the other hand, higher or lower temperatures can be utilized.

Generally, it is preferred to carry out this reaction at a temperature of from 0° C. to 60° C.

On the other hand, the compound of formula VII can be prepared from the compound of formula IV by reacting the compounds of formula IV with a compound of the formula:

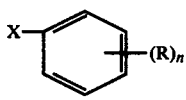

wherein R and n are as above.

The compounds of formulas IV and X are reacted to form the compound of formula VIII utilizing a copper catalyst. This reaction is carried out in an inert organic solvent in the presence of an alkali metal base. In carrying out this reaction, any conventional inert organic solvent can be utilized. Among the preferred solvents are nitrobenzene, collidine, diglime and tertiary amines. Among the tertiary amines are included the cyclic tertiary amines such as pyridine and the tri-lower alkyl amines such as trimethyl amine, triethyl amine, etc. This reaction is also carried out in the presence of an alkali metal base. Among the preferred bases are included the alkali methyl hydroxides such as lithium, potassium and sodium hydroxide, as well as the alkali carbonates and bicarbonates such as sodium carbonate, potassium carbonate, sodium bicarbonate and potassium bicarbonate. The preferred inorganic base for utilization in this reaction is a weak base such as potassium carbonate. In carrying out this reaction, temperature and pressure are not critical and this reaction can be carried out at room temperature and atmospheric pressure. However, if desired, elevated temperatures can be utilized. Generally, it is preferred to utilize temperatures of from 100° to 250° C. in carrying out this reaction. This reaction takes place in the presence of a copper catalyst such as cupric chloride, cupric bromide, cupric sulfate, cuprous iodide, a mixture of copper-bronze and the metallic copper, etc. with granular copper being preferred.

The compound of formula VIII is converted to the compound of formula V by treating the compound of formula VIII with a formylating agent. In carrying out this reaction, any conventional formylating agent can be utilized. Among the preferred formylating agents are chloral, ethyl formate, etc. Generally, this reaction is carried out without or in an inert organic solvent. Any conventional inert organic solvent can be utilized. Among the preferred inert organic solvents are included chloroform. In carrying out this reaction, temperature and pressure are not critical. This reaction can be carried out at room temperature and atmospheric pressure. On the other hand, lower or higher temperatures can be utilized.

In accordance with the invention, the compounds of formula IV can be converted to the compound of formula V via the following intermediate

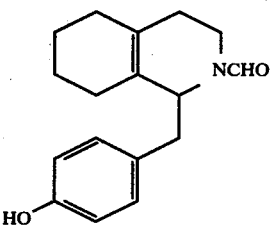

The compound of formula IV is converted to the compound of formula XI by formylation as described in connection with the formylation of a compound of formula VIII to produce a compound of formula V.

The compound of formula XI can be converted to the compound of formula V by treating the compound of formula XI with the compound of formula X in the same manner as described in connection with the reaction of the compound of formula X with the compound of formula IV to produce the compound of formula VIII. The same conditions described hereinbefore in connection with the reaction of a compound of formula IV to produce a compound of formula VIII can be utilized to affect this conversion.

The compound of formula V can be coverted to a compound of the formula I-A above via an intermediate of the formula:

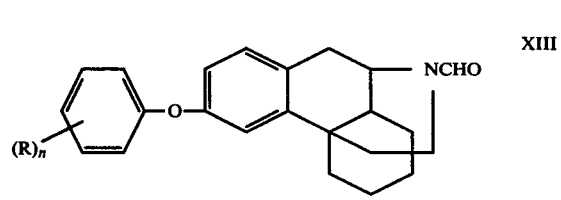

wherein R and n are as above.

The compound of formula V can be converted to the compound of formula XIII by treating the compound of formula V with a strong acid. Any conventional strong acid can be utilized to carry out this conversion. Among the strong acids are included the inorganic mineral acids, the Lewis acids and trifluoroacetic acid. Among the inorganic mineral acids, phosphoric acid and sulfuric acid are preferred. Among the Lewis acids, aluminum chloride, borontrifluoride etherate, zinc chloride, etc. are preferred. In carrying out this reaction, there is no need for using an inert organic solvent since the acid medium itself can be utilized as the solvent. If desired, however, any conventional inert organic solvent may be utilized in the reaction medium. In carrying out this reaction, temperature and pressure are not critical and generally it is preferred to utilize room temperature and atmospheric pressure in carrying out this invention. However, if desired, elevated temperatures can be utilized. Generally it is preferred to carry out this reaction at a temperature of from 50° C. to 100° C.

The compound of formula XIII can be converted to the compound of formula I-A by reduction. Any conventional means of reducing an n-formyl group to a corresponding N-methyl group can be utilized in carrying out this reaction. Generally, this reduction is carried out by utilizing a lithium aluminum hydride reducing agent. Any of the conditions hereinbefore described in connection with reduction by use of lithium aluminum hydride can be utilized in carrying out this reaction.

The compound of formula I-A can be resolved into the optical isomer of formula I by any conventional method of optical resolution. Among the preferred methods of optical resolution is by treating the compound of formula I-A with a acid resolving agent such as tartaric acid, mandelic acid, camphor sulfonic acid, dibenzoyl tartaric acid and gulonic acid. Any of the conventional methods of utilizing these acid resolving agents can be utilized to convert the compound of formula I-A to the compound of formula I.

The compound of formula VIII may be in the form of the free bases or can be utilized as a salt with any of the aforementioned pharmaceutically acceptable acids in the process of this invention.

The following examples are illustrative but not limitative of the invention. In the Examples, all temperatures are in degrees Centigrade. The term "concentrated ammonium hydroxide" designates an aqueous solution containing 33° by weight of ammonia. The term "concentrated sulfuric acid" designates an aqueous solution of sulfuric acid containing 37° by weight sulfuric acid. The term "petroleum ether" designates a petroleum ether having a boiling point of about 60° C.

EXAMPLE 1

(±)-1-(p-Hydroxybenzyl)-2-formyl-1,2,3,4,5,6,7,8-octahydroisoquinoline

To a mixture of 30.0 g (0.12 mol) of (±)-1-(p-hydroxybenzyl)-1,2,3,4,5,6,7,8-octahydroisoquinoline and 75 ml of chloroform was added dropwise to a solution of 19.2 g of trichloroacetaldehyde in 30 ml of chloroform. After the mixture had been stirred for 16 hrs at room temperature it was diluted with 150 ml of chloroform and washed with 4 N aqueous hydrochloric acid (50 ml) and water (50 ml). After drying, the solvent was removed under reduced pressure to give a residue, which after crystallization from ethyl acetate afforded 33.1 g (98%) of pure (±)-1-(p-hydroxybenzyl)-2-formyl-1,2,3,4,5,6,7,8-octahydroisoquinoline, mp 154°-156°. For analysis a sample of this compound was recrystallized from ethyl acetate, mp 161°-162°.

EXAMPLE 2

(±)-1-(p-Phenoxybenzyl)-1,2,3,4,5,6,7,8-octahydroisoquinoline oxalate

A mixture of 4.8 g (0.019 mol) of (±)-1-(p-hydroxybenzyl)-1,2,3,4,5,6,7,8-octahydroisoquinoline and 100 ml of freshly distilled pyridine was heated at 110°-120° (bath temp.) with stirring under nitrogen with 2.4 ml of bromobenzene, 9.6 g of copper (granular) and 4.2 g of potassium carbonate for 8 days. The mixture was filtered and the filtrate was concentrated under reduced pressure. The residue was partitioned between diethyl ether (150 ml) and 4 N aqueous sodium hydroxide (200 ml). The ether solution was washed with water and dried. Removal of the solvent gave 2.75 g of crude product, which on treatment with oxalic acid (0.8 g) in diethyl ether (30 ml) gave the crude oxalate salt (±)-1-(p-phenoxybenzyl)-1,2,3,4,5,6,7,8-octahydroisoquinoline oxalate. Crystallization of this compound from ethanol afforded 2.8 g (34%) of pure (±)-1-(p-phenoxybenzyl)-1,2,3,4,5,6,7,8-octahydroisoquinoline oxalate, mp 177°-179°.

EXAMPLE 3

(±)-1-(p-Phenoxybenzyl)-1,2,3,4,5,6,7,8-octahydroisoquinoline

A 0.4 g (0.001 mole) sample of the (±)-1-(p-phenoxybenzyl)-1,2,3,4,5,6,7,8-octahydroisoquinoline oxalate was suspended in water and the suspension was basified with conc. aqueous ammonium hydroxide. The aqueous suspension was extracted with diethyl ether (2×20 ml), and the ether solution was washed with water and dried (MgSO4). Removal of the solvent gave 0.3 g (97%) of (±)-1-(p-phenoxybenzyl)-1,2,3,4,5,6,7,8-octahydroisoquinoline. For analysis, a sample of this compound was distilled, bp 185°-195°. (0.1 mm Hg).

EXAMPLE 4

(±)-1-(p-Phenoxybenzyl)-2-formyl-1,2,3,4,5,6,7,8-octahydroisoquinoline

A solution of 29.0 g (0.106 mol) of (±)-1-(p-hydroxybenzyl)-2-formyl-1,2,3,4,5,6,7,8-octahydroisoquinoline in 530 ml of freshly distilled pyridine was refluxed with stirring under nitrogen with 12.88 ml of bromobenzene, 51.5 g of copper (granular) and 22.55 g of potassium carbonate for 14 days. The reaction mixture after cooling was diluted with ether 1 l. and filtered. The filtrate was concentrated under reduced pressure and the residue was dissolved in ether (300 ml). The ether solution was washed with 4 N aqueous sodium hydroxide (200 ml) then with water and dried. Removal of the solvent under reduced pressure gave 25.8 g (69%) of crude (±)-1-(p-phenoxybenzyl)-2-formyl-1,2,3,4,5,6,7,8-octahydroisoquinoline. For analysis, a sample of this compound was distilled, bp 220°-230° (0.05 mm Hq).

EXAMPLE 5

(±)-1-(p-Phenoxybenzyl)-2-formyl-1,2,3,4,5,6,7,8-octahydroisoquinoline

To a solution of 0.78 g (0.002 mol) of (±)-1-(p-phenoxybenzyl)-1,2,3,4,5,6,7,8-octahydroisoquinoline in 5 ml of chloroform was added 0.42 g of chloral in 1 ml of chloroform dropwise. After the mixture had been stirred at room temperature for 3 hrs it was diluted with 15 ml of chloroform and washed with 4 N hydrochloric acid (10 ml) and water (10 ml). After drying, the solvent was removed under reduced pressure to give 0.81 g (96%) of crude (±)-1-(p-phenoxybenzyl)-2-formyl-1,2,3,4,5,6,7,8-octahydroisoquinoline. For characterization, a sample of this compound was distilled, bp 225°-227° (0.08 mm Hq).

EXAMPLE 6

N-[2-(1-Cyclohexen-1-yl)ethyl]-4-phenoxyphenyl acetamide

A mixture of 1.26 g (0.01 mol) of cyclohexen (1)-yl-ethylamine and 1.9 g of 4-phenoxyphenylacetic acid in 20 ml of xylene was heated at reflux for 16 hrs with removal of the water by means of a Dean-Stark apparatus. After evaporation of the solvent, the crude product was crystallized from cyclohexane-hexane mixture to give 2.6 g (76%) of pure N-[2-(1-cyclohexen-1-yl)ethyl]-4-phenoxyphenyl acetamide, mp 74°-75°.

EXAMPLE 7

(±)-1-(p-Phenoxybenzyl)-1,2,3,4,5,6,7,8-octahydroisoquinoline

A mixture of 2.5 g (0.01 mol) N-[2-(1-cyclohexen-1-yl)ethyl]-4-phenoxyphenyl acetamide, 5.0 ml of POCl$_3$ and 20 ml of toluene was heated at reflux under nitrogen for 2 hrs. After evaporation of the solvent and excess reagent there was obtained (±)-1-(p-phenoxybenzyl)-3,4,5,6,7,8-hexahydroisoquinoline as residue. The residue was triturated with pet ether (2×10 ml). The pet ether insoluble hexahydro compound was dissolved in methanol and immediately reduced by portionwise addition of 1.0 g of sodium borohydride. The reaction mixture was stirred at room temperature for 4 hrs. The methanol was distilled off and the residue was partitioned between ether (60 ml) and dilute aqueous ammonium hydroxide. The ether solution was washed with water, dried and evaporated to give 1.6 g (69%) of crude (±)-1-(p-phenoxybenzyl)-1,2,3,4,5,6,7,8-octahydroisoquinoline.

For purification, 1.5 g (0.005 mole) of the above crude (±)-1-(p-phenoxybenzyl)-1,2,3,4,5,6,7,8-octahydroisoquinoline in 5 ml of acetone was treated with 0.42 g of oxalic acid and allowed to crystallize. The crude oxalate was recrystallized from ethanol (30 ml) to give 1.61 g (84%) of pure (±)-1-(p-phenoxybenzyl)-1,2,3,4,5,6,7,8-octahydroisoquinoline oxalate, mp 176°–178°.

EXAMPLE 8

(±)-3-Phenoxy-N-formylmorphinan (±)-1-(p-Phenoxybenzyl)-2-formyl-1,2,3,4,5,6,7,8-octahydroisoquinoline, 24.5 g (0.07 mol), was combined under stirring with 120 g of phosphoric acid which had been mixed with 1.0 g of concentrated sulfuric acid and the mixture was heated in a nitrogen atmosphere to 70°. The resulting homogeneous solution was kept at 70° for 48 hrs. The mixture was cooled in an ice bath and ice-water was added. The resulting suspension was extracted with ethyl acetate (100 ml). The ethyl acetate solution was washed with water and dried. Removal of the solvent gave 23.3 g (95%) of crude (±)-3-phenoxy-N-formylmorphinan.

For characterization a sample of the morphinan was isolated from the above mixture by preparative tlc on silica gel (eluted with ethyl acetate) and distilled, bp 210°–220° (0.1 mm Hq).

EXAMPLE 9

(±)-3-Phenoxy-N-methylmorphinan

To a suspension of 1.1 g of lithium aluminum hydride in 120 ml of anhydrous tetrahydrofuran, 10.8 g (0.03 mol) of crude (±)-3-phenyl-N-formylmorphinan in 50 ml of tetrahydrofuran was added dropwise. After the mixture had been refluxed for 3 hrs, it was cooled to room temperature and ethyl acetate followed by water were added dropwise. The resulting suspension was dried, filtered and the filtrate concentrated in vacuo to give a dark brown oil which was distilled, bp 170°–180° (0.05 mm Hq) to afford 7.6 g (73%) of crude (±)-3-phenoxy-N-methylmorphinan.

This crude morphinan, 7.6 g (0.02 mole) on treatment with oxalic acid (2.4 g) in ether (40 ml) afforded 6.8 g of crude oxalate mp 110°–120° (d). Several recrystallizations from acetonitrile gave 3.6 g (37%) of pure (±)-3-phenoxy-N-methylmorphinan oxalate, mp 144°–146°.

EXAMPLE 10

Resolution of (±)-3-Phenoxy-N-methylmorphinan 2.0 g (0.006 mol) of (±)-3-Phenoxy-N-methylmorphinan was dissolved in 5 ml of hot ethanol (abs.) and combined with a hot solution of 0.9 g of d-tartaric acid in 5 ml of ethanol (abs.) The resulting solution was seeded with (−)-3-phenoxy-N-methylmorphinan d-tartrate and then allowed to stand at room temperature for 48 hrs. The crystals were collected by filtration, washed with ethanol and dried, thus affording 0.95 g (68%) of crude salt, mp 106–1100, [α]$^{25}$D −17.9° (c 1.0, MeOH). Recrystallization from ethanol (5 ml) yielded 0.485 g (35%) of pure (−)-3-phenoxy-N-methylmorphinan d-tartrate as a solid mp 131°14 133°, [α]$^{25}$D−20.2° (c 1.0, MeOH), melted undepressed on admixture with an authentic sample of (−)-3-phenoxy-N-methylmorphinan d-tartrate.

EXAMPLE 11

A tablet was formulated as follows:

| Item | Ingredient | Mg/tablet |
| --- | --- | --- |
| 1. | (±)-3-phenoxy-N-methyl-morphinan | 10.0 |
| 2. | Lactose anhydrous | 103.0 |
| 3. | Avicel * | 45.0 |
| 4. | Modified starch | 10.0 |
| 5. | Corn starch | 30.0 |
| 6. | Magnesium stearate | 2.0 |
|  | Weight of tablet | 300 mg |

Procedure

1. Mix items 1,2,3,4 and 5 in a suitable mixer for 10 to 15 minutes.
2. Add magnesium stearate (item 6) as a premix and mix for 4 minutes. Compress on a suitable press.

EXAMPLE 12

Tablet was formulated as follows:

| Item | Ingredient | mg/tablet |
| --- | --- | --- |
| 1. | (±)-3-phenoxy-N-methyl morphinan | 5.0 |
| 2. | Lactose | 99.0 |
| 3. | Pregelatinized starch | 10.0 |
| 4. | Corn Starch | 15.0 |
| 5. | Modified starch | 10.0 |
| 6. | Magnesium stearate | 1.0 |
|  | Weight of Tablet | 140 mg |

Procedure

1. Mix items 1,2,3,4 and 5 in a suitable mixer, granulate with water. Dry over night in an oven. Mill through a Fitzpatrick mill.
2. Mix with item 6 and compress on a suitable press.

EXAMPLE 13

A capsule Formulation

| Item | Ingredient | mg/capsule |
| --- | --- | --- |
| 1. | (±)-3-phenoxy-N-methyl-morphinan | 10.0 |
| 2. | Lactose | 218.0 |
| 3. | Corn Starch | 50.0 |
| 4. | Magnesium stearate | 2.0 |
| 5. | Talc | 10.0 |

| Item | Ingredient | mg/capsule |
|---|---|---|
| | Fill weight of capsule | 220 mg |

Procedure

1. Mix items 1,2, and 3 in a suitable mixer. Mill through suitable mill.

2. Mix with items 4 and 5 and fill on capsule machine.

I claim:

1. A compound of the formula:

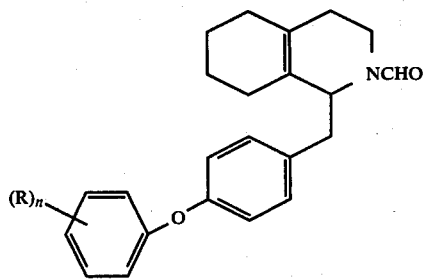

wherein R is halo, lower alkyl, nitro, lower alkoxy, hydroxy or hydrogen; and n is an integer from 1 to 5.

2. The compound of claim 1 wherein said compound is (±)-1-(p-phenoxybenzyl)-N-formyl-1,2,3,4,5,6,7,8-octahydroisoquinoline.

3. A racemic compound of the formula:

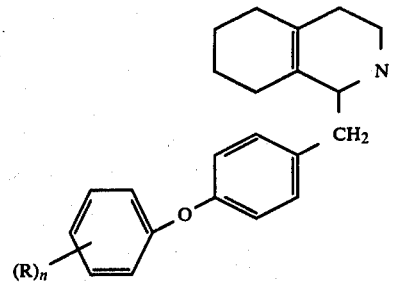

wherein R is halo, lower alkyl, nitro, lower alkoxy, hydroxy or hydrogen; and n is an integer from 1 to 5.

4. The compound of claim 3 wherein said compound is (±)-1-(p-phenoxybenzyl)-1,2,3,4,5,6,7,8-octahydroisoquinoline oxalate.

5. A compound of the formula:

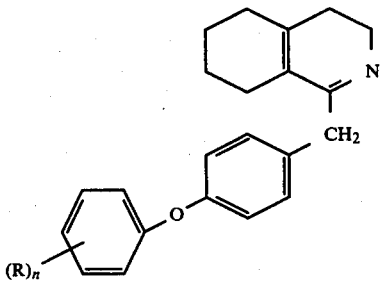

wherein R is halo, lower alkyl, nitro, lower alkoxy, hydroxy or hydrogen; and n is an integer from 1 to 5.

6. The compound of claim 5 wherein siad compound is (±)-1-(p-phenoxybenzyl)-3,4,5,6,7,8-hexahydroisoquinoline.

* * * * *